United States Patent
Okumura et al.

(10) Patent No.: US 10,143,429 B2
(45) Date of Patent: Dec. 4, 2018

(54) X-RAY DIAGNOSTIC DEVICE

(71) Applicant: SHIMADZU CORPORATION, Kyoto (JP)

(72) Inventors: Hiroshi Okumura, Kyoto (JP); Toru Hayakawa, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 200 days.

(21) Appl. No.: 15/426,584

(22) Filed: Feb. 7, 2017

(65) Prior Publication Data

US 2018/0220981 A1    Aug. 9, 2018

(51) Int. Cl.
*A61B 6/00* (2006.01)

(52) U.S. Cl.
CPC ............... *A61B 6/44* (2013.01); *A61B 6/487* (2013.01)

(58) Field of Classification Search
None
See application file for complete search history.

(56) References Cited

U.S. PATENT DOCUMENTS

| | | | | |
|---|---|---|---|---|
| 2009/0257561 A1* | 10/2009 | Okuno | ........... | A61B 6/4233 378/116 |
| 2011/0249805 A1* | 10/2011 | Kralles | ........... | A61B 6/4405 378/198 |
| 2013/0077737 A1* | 3/2013 | Fasoli | ........... | G01N 23/04 378/4 |
| 2016/0089093 A1* | 3/2016 | Mao | ........... | A61B 6/4441 378/198 |

FOREIGN PATENT DOCUMENTS

| | | |
|---|---|---|
| JP | 2016036670 | 3/1916 |
| JP | H04-096736 | 3/1992 |
| JP | 2011-041624 | 3/2011 |

* cited by examiner

*Primary Examiner* — Hoon K Song
(74) *Attorney, Agent, or Firm* — Andrew F. Young, Esq.; Lackenbach Siegel, LLP (57) ABSTRACT

An X-ray diagnostic device has an attachment-and-detachment detection element that detects an attachment-and-detachment of the attachment-and-detachment member, a rotation detection element that detects the rotation of the motor, a torque adjustment element that adjusts the torque of the motor, and a torque detection element that detects the torque when the rotation of the motor suspends; wherein when attachment-and-detachment is detected, the brake is released; when the brake is released, the rotation of the motor due to an out of balance condition between the up-and-down moving element and the counterweight is detected and the motor torques is adjusted so as to suspend the detected rotation of the motor; the torque when the rotation of the motor suspends is continuously provided, so that the balance between the up-and-down moving element and the counterweight can be kept positioned.

4 Claims, 6 Drawing Sheets

X-RAY DIAGNOSTIC DEVICE

CROSS REFERENCE TO RELATED APPLICATIONS

This application relates to, but does not claim priority from, JP 2014463696 filed Aug. 11, 2014, the entire contents of which are incorporated herein by reference.

FIGURE SELECTED FOR PUBLICATION

Figure 2:
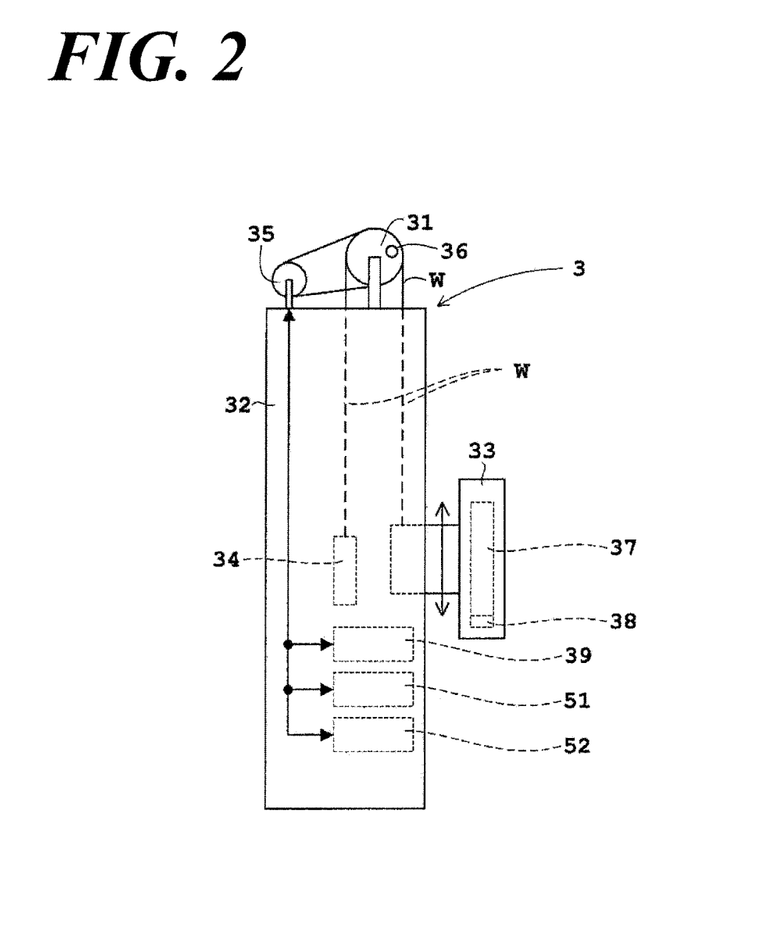
FIG. 2 is a schematic view and a block diagram illustrating the X-ray imaging unit of the X-ray imaging device according to the aspect of the Embodiment 1.

FIG. 2

BACKGROUND OF THE INVENTION

Field of the Invention

The present invention relates to an X-ray diagnostic device and particularly relates to the X-ray diagnostic device having the structure capable of holding balance.

Description of the Related Art

Conventionally, as such device, a device including: a fixing element (up-and-down moving means) being held by a wire from a pulley to be freely movable up-and-down; and a weight (counterweight), which is connected to the opposite end of one end of fixed side of wire (side of up-and-down moving means), to make a balance between the fixing element (up-and-down moving means) and the weight-balance through the pulley; and thereby the balance between the fixing element (up-and-down moving means) and the weight (counterweight) (e.g., Patent Document 1). For example, when a plane detection unit as a removable member is adopted and the plane detection unit is mounted and fixed to the fixing element, the weight per se is set so as to keep the weight-balance (i.e., balanced state) between the fixing element and the plane detection unit and the weight. Accordingly, when the plane detection unit is removed from the fixing element, the weight-balance becomes out of balance, so that the fixing element should lift up.

Then, according to Patent Document 1 (Laid Open JP 2011-041624, the contents of which are incorporated herein fully by reference to describe the same), the rotation torque thereof is changed by changing the diameter of the pulley so as to keep the balance thereof. Specifically, when the plane detection unit is removed from the fixing element, the diameter of the pulley hanging the weight is made small as if the rotation torque of the weight becomes equal to the rotation torque of only fixing element. As to the other aspect, it is disclosed that an X-ray tube is positioned at an arbitrary height as a mechanism to keep the balance through the pulley relative to the mechanism having a counterweight (e.g., Patent Document 2).

RELATED PRIOR ART DOCUMENTS

Patent Documents

Patent Document 1: Laid Open JP 2011-041624
Patent Document 2: Laid Open JP H04-096736

ASPECTS AND SUMMARY OF THE INVENTION

Problems to be Solved by the Invention

However, the following problems (i)-(iv) are remained to be solved in the conventional example according to the aspect of the above Patent Document 1, Laid Open JP 2011-041624. Specifically, (i) According to a mechanism in which the diameter of the rotatable unit (pulley) is changed to adjust the rotation torque of the weight, the mechanism per se and the apparatus may be bulky because the diameter of the large rotation unit must be assured and the mechanism to change the diameter thereof must be required. (ii) A weight of the attachment-and-detachment member to be attached and detached (e.g., a plane detector unit) must be determined in advance. (iii) It is structure-wise difficult to correspond to attachment-and-detachment relative to a plurality of kinds of attachment-and-detachment parts (e.g., plane detection unit) having a different weight each other, for example, depending on a size, a manufacturer and so forth (i.e., for example, it is difficult to switch the diameter of pulley depending on a variety of steps). (iv) It is problematic; that depending on difference between units, the balance is too hard to be maintained preciously, so that a calibration is required unit by unit.

In addition, the above Patent Document 2 (JP H04-096736, the entire contents of which are incorporated herein by reference to fully disclose the same) discloses no mechanism that can provide a torque for the motor when the weight-balance becomes out of balance and no measures when the weight-balance becomes out of balance.

The present invention is motivated under consideration of such circumstance and a purpose of the present invention is to provide an X-ray diagnostic device, wherein no bulky mechanisms is required (i), a weight, a kind and a number of the attachment-and-detachment member to be attached thereto and detached therefrom is not mandatory to be figured out in advance (ii) (iii), and no calibration is required unit by unit (iv).

Means to Solve the Objects

The present invention comprises the following structure to solve such problem.

Specifically, an X-day diagnostic device that performs an X-ray diagnosis and is now referred as the X-ray diagnostic device according to the present invention (hereafter the first invention) comprises: a pulley; a pulley holding means that holds the pulley; an up-and-down moving means that is held freely movable in the up-and-down direction with a wire from the pulley; a counterweight that makes a weight-balance with the up-and-down moving means through the pulley, wherein the counterweight is connected to one opposite end of the wire of which the other end is in the side of the up-and-down moving means; a motor that drives the pulley; a brake that suspends the rotation of the pulley; and an attachment-and-detachment member relative to the up-and-down moving means; and further comprises: an attachment-and-detachment detection means that detects attachment-and-detachment of the attachment-and-detachment member; a rotation detection means that detects rotation of the motor; a torque adjustment means that adjusts the torque of the motor; and a torque detection means that detects the torque when the rotation of the motor suspends; wherein when attachment-and-detachment is detected by the attachment-and-detachment detection means, the brake is released and the rotation detection means detects the rotation of the motor along with the rotation of the pulley due to out-of-balance between the up-and-down moving means and the counterweight when the brake is released, the rotation detection means adjust the torque of the motor so as to suspend the rotation of the motor detected by the rotation detecting means; and the torque is continuously provided for the motor when the rotation of the motor detected by the torque detection means suspends, so that the balance between the up-and-down moving means and the counterweight can be being kept.

[Action and Effect] According to the aspect of the present invention, the X-ray diagnostic device (the first invention) comprises the attachment-and-detachment detection means that detects attachment and detachment of the attachment-and-detachment member, so that the attachment-and-detachment detection means can detect out of weight-balance between the up-and-down moving means and the counterweight by attachment and detachment of the attachment-and-detachment member. When attachment and detachment is detected by the attachment-and detachment detection means under releasing the brake to suspend rotation of the pulley, the motor (to drive the pulley) rotates along with rotation of the pulley due to the above out of weight-balance (i.e., out of balance). At this time, the rotation detection means that detects the rotation of the motor and torque adjustment means that adjusts the torque of the motor are equipped, so that the torque adjustment means adjusts the torque of the motor so as to suspend the rotation of the motor detected by the rotation detection means. In addition, the torque detection means that detects the torque when the rotation of the motor suspends is equipped, so that the torque at which the rotation of the motor detected by the torque detection means suspends can be provided continuously and the balance between the up-and-down moving means and the counterweight can be kept.

In such way, even though any member of the attachment-and-detachment members is either attached or detached, it is not necessary for the moving to be locked because of out of balance between the up-and-down moving means and the counterweight and when the moving is allowed under the out of balance, uncontrollable moving of the up-and-down moving means in the up-and-down direction may not expose an operator and a patient to risk and further a light work can be operational. In addition, when the attachment-and-detachment member is attached to or detached from the up-and-down moving means, the torque can be adjusted arbitrarily (as the motor suspends) corresponding to the weight, the kind and the number of the attachment-and-detachment member, so that the weight, the kind and the number of the attachment-and-detachment member to be attached or detached may not be mandatory to be figured out in advance (ii) (iii). In addition, rotation of the motor suspends by adjusting the torque and the balance can be kept, so that the mechanism cannot be bulky because a large diameter of the rotation unit is not required to be assured or the diameter update mechanism is not required as required in conventional ways (i). In addition, as the torque can be adjusted regardless the difference between individuals so that the rotation of the motor suspends and the balance is being kept, no calibration is required unit by unit (iv). As results, no bulky mechanisms is required (i); the weight, the kind and the number of the attachment and detachment members to be attached or detached is not mandatory to be figured out in advance (ii) (iii); and no calibration is required unit by unit (iv).

In addition, an X-ray diagnostic device that performs an X-ray diagnosis and is now referred as the X-ray diagnostic device according to the aspect of the different invention from the first invention (hereafter the second invention) comprises: a pulley; a pulley holding means that holds the pulley; an up-and-down moving means that is held freely movable in the up-and-down direction with a wire from the pulley; a counterweight that makes a weight-balance with the up-and-down moving means through the pulley, wherein the counterweight is connected to one opposite end of the wire of which the other end is in the side of the up-and-down moving means; a motor that drives the pulley; a brake that suspends the rotation of the pulley; and an attachment-and-detachment member that is attached or detached relative to the up-and-down moving means, and further comprises: a rotation detection means that detects the rotation of the motor; a torque adjustment means that adjusts the torque of the motor; a torque detection means that detects the torque when the rotation of the motor suspends; wherein the brake is released and then the brake is operated in order; the rotation detection means detects the rotation of the motor along with the rotation of the pulley due to out of balance between the up-and-down moving means and the counterweight when the brake is released; the torque adjustment means adjust the torque so as to suspend the rotation of the motor which is detected by the rotation detection means; and the balance between the up-and-down moving means and the counterweight is being kept by continuously providing the torque, which is detected by the torque detection means when the rotation of the motor suspends.

[Action and Effect] According to the aspect of the present invention, the X-ray diagnostic device (the second invention) comprises no attachment-and-detachment detection means according to the aspect of the first invention, which is different from the first invention, and the brake is released and then the brake is operated in order. Accordingly, when the brake is released, the motor (driving the pulley) rotates along with the rotation of the pulley due to the out of balance between the up-and-down moving means and the counterweight. And as well as the aspect of the first invention, the rotation detection means that detects the rotation of the motor and the torque adjustment means that adjusts the torque of the motor are equipped, so that the torque adjustment means adjusts the torque of the motor so as to suspend the rotation of the motor detected by the rotation detection means. In addition, as well as the aspect of the first invention, the torque detection means that detects the torque when the rotation of the motor suspends is equipped, so that the torque at which the rotation of the motor detected by the torque detection means suspends can be provided continuously and the balance between the up-and-down moving means and the counterweight can be kept.

In such way, it is different from the aspect of the first invention that when the brake is released and even if the pulley and the motor rotate due to the out of balance between the up-and-down moving means and the counterweight, the torque is adjusted so as to suspend the rotation of the motor, so that the adjusted torque can be continuously provided to keep the balance. Accordingly, even when the brake is released, it is not necessary for the moving to be locked because of the out of balance between the up-and-down moving means and the counterweight, and when the moving is allowed under the out of balance as well as the first invention, uncontrollable moving of the up-and-down moving means may not expose an operator and a patient to risk and further a light work can be operational. In addition, when the brake is released, the torque can be adjusted arbitrarily (as the rotation of the motor suspends) corresponding to the weight, the kind and the number of the attachment and detachment member, so that the weight, the kind and the number of the attachment and detachment members to be attached thereto and detached therefrom may not be mandatory to be figured out in advance (ii) (iii) as well as the first invention. In addition, the rotation of the motor suspends due to adjusting the torque and the balance can be kept as well as the first invention, so that the mechanism cannot be bulky (i) because a large diameter of the rotation unit is not required to be assured or the diameter update mechanism is not required as required in conventional ways. In addition, as the torque can be adjusted regardless the difference between individuals as well as the first invention, the rotation of the motor suspends and the balance is being kept, so that no calibration is required unit by unit (iv). As results, no bulky mechanisms is required (i); the weight, the kind and the number of the attachment-and-detachment members to be attached and detached is not mandatory to be figured out in advance (ii) (iii); and no calibration is required unit by unit (iv).

According to the aspect of the second invention, even when an operator instructs to initiate releasing the brake and, at the same time, the rotation detection means can be operative to detect the rotation of the motor, a time-lag may take place between the initiation directive to release the brake and the detection of the rotation of the motor by the rotation detection means. Therefore, according to the aspect of the second invention, it is preferable that a timer capable of monitoring the time when the brake is released temporarily is equipped and the rotation detection means can detect the rotation of the motor along with the rotation of the pulley due to the out of balance between the up-and-down moving means and the counterweight when the brake is released by the timer. If such timer is equipped, an incident of the time-lag can be prevented and the balance can be more preciously controlled.

In addition, an X-day diagnostic device that performs an X-ray diagnosis and is now referred as the X-ray diagnostic device according to the aspect of the different invention from the first invention and the second invention (hereafter the third invention) comprises: a pulley; a pulley holding means that holds the pulley; an up-and-down moving means that is held freely movable in the up-and-down direction with a wire from the pulley; a counterweight that makes a weight-balance with the up-and-down moving means through the pulley, wherein the counterweight is connected to one opposite end of the wire of which the other end is in the side of the up-and-down moving means; a brake that suspends the rotation of the pulley; an attachment-and-detachment member that is attached and detached relative to the up-and-down moving means, a loading detection means that detects weight variation due to the attachment-and-detachment of the attachment-and-detachment member; a tank that provides the weight variation in association with the up-and-down moving means and the counterweight; a pump that conveys the fluid inside the tank between the tank located in the side of the up-and-down moving means and the tank located in the side of the counterweight; wherein the pump is driven to flow the fluid in the direction to set off the weight variation between two tanks so that the balance between the up-and-down moving means and the counterweight can be kept when the loading detection means detects the weight variation due to attachment-and-detachment of the attachment-and-detachment member.

[Action and Effect] According to the aspect of the present invention, the X-ray diagnostic device (the third invention) comprises none of the attachment-and-detachment detection means according to the aspect of the first invention, which is different from the first invention, the rotation detection means, the torque adjustment means and the torque detection means, which are different from the first invention the second invention, but comprises a loading detection means that detects the weight variation due to the attachment-and-detachment of the attachment-and-detachment member. Therefore the loading detection means detects out of weight-balance between the up-and-down moving means and the counterweight due to the attachment-and-detachment of the attachment-and-detachment member. Followingly, the tank that provides the weight variation in association with the up-and-down moving means and the counterweight and the pump that conveys the fluid inside the tank between the tank located in the side of the up-and-down moving means and the tank located in the side of the counterweight are equipped, which is different from the first invention and the second invention. In addition, the pump is driven to flow the fluid in the direction to set off the weight variation between two tanks so that the balance between the up-and-down moving means and the counterweight can be kept when the loading detection means detects the weight variation due to attachment-and-detachment of the attachment-and-detachment member.

In such way, differently from the first invention and the second invention, the pump is operative corresponding to weight variation detected by the loading detection means and the fluid flows in the direction so as to set off the weight variation between two tanks so that the balance can be kept. Therefore, even though any member of the attachment-and-detachment members is either attached or detached as well as the first invention, it is not necessary for the moving to be locked because of the out of balance between the up-and-down moving means and the counterweight and when the moving is allowed under the out of balance, uncontrollable moving of the up-and-down moving means in the up-and-down direction may not expose an operator and a patient to risk and further a light work can be operational. In addition, the fluid flows in according with the weight variation, so that the weight, the kind and the number of the attachment and detachment members to be attached thereto and detached therefrom may not be mandatory to be figured out in advance (ii) (iii) as well as the first invention and the second invention. In addition, the balance can be kept by moving the fluid in accordance with the weight variation so that the mechanism cannot be bulky (i) because a large diameter of the rotation unit is not required to be assured or the diameter update mechanism is not required, as well as the first invention and the second invention, but such aspects are required in conventional way. In addition, the fluid moves corresponding to the weight variation at that time to keep the balance therefor so that no calibration can be required unit by unit as well as the first invention and the second invention. As results, no bulky mechanisms is required (i); the weight, the kind and the number of the attachment-and-detachment members to be attached and detached is not mandatory to be figured out in advance (ii) (iii); and no calibration is required unit by unit (iv).

Effect of the Invention

The X-ray diagnostic device (the first invention) according to the aspect of the present invention comprises: an attachment-and-detachment detection member that detects attachment-and-detachment of the attachment-and-detachment member; a rotation detection means that detects rotation of the motor; a torque adjustment means that adjusts the torque of the motor; a torque detection means that detects the torque when the rotation of the motor suspends.

The brake is released when attachment-and-detachment is detected by the attachment-and-detachment detection means, and the rotation of the motor along with the rotation of the pulley due to out of balance between the up-and-down moving means and the counterweight. And the torque adjustment means adjusts so as to suspend the rotation of the motor detected by the rotation detection means. And the torque at which the rotation of the motor detected by the torque detection means suspends can be provided continuously, so that the balance between the up-and-down moving means and the counterweight can be kept. As results, no bulky mechanisms is required (i); the weight, the kind and the number of the attachment-and-detachment members to be attached and detached is not mandatory to be figured out in advance (ii) (iii); and no calibration is required unit by unit (iv).

In addition, the X-ray diagnostic device (the second invention) according to the aspect of the present invention comprises: the rotation detection means that detects rotation of the motor; the torque adjustment means that adjusts the torque of the motor; and the torque detection means that detects the torque when the rotation of the motor suspends. A brake release and a brake operation are conducted in order and the rotation detection means detects the rotation of the motor along with the rotation of the pulley due to the out of balance between the up-and-down moving means and the counterweight. And the torque adjustment means adjusts so as to suspend the rotation of the motor detected by the rotation detection means. And the torque at which the rotation of the motor detected by the torque detection means suspends can be provided continuously, so that the balance between the up-and-down moving means and the counterweight can be kept. As results, no bulky mechanisms is required (i); the weight, the kind and the number of the attachment-and-detachment members to be attached and detached is not mandatory to be figured out in advance (ii) (iii); and no calibration is required unit by unit (iv).

In addition, the X-ray diagnostic device (the third invention) according to the aspect of the present invention comprises: the loading detection means that detects the weight variation due to attachment-and-detachment of the attachment-and-detachment member; the tank that provides the weight variation in association with the up-and-down moving means and the counterweight; and the pump that conveys the fluid inside the tank between the tank located in the side of the up-and-down moving means and the tank located in the side of the counterweight. When the loading detection means detects the weight variation due to attachment-and-detachment of the attachment-and-detachment member, the pump is driven to flow the fluid in the direction to set off the weight variation between two tanks so that the balance between the up-and-down moving means and the counterweight can be kept. As results, no bulky mechanisms is required (i); the weight, the kind and the number of the attachment-and-detachment members to be attached and detached is not mandatory to be figured out in advance (ii) (iii); and no calibration is required unit by unit (iv).

The above and other aspects, features and advantages of the present invention will become apparent from the following description read in conjunction with the accompanying drawings, in which like reference numerals designate the same elements.

DETAILED DESCRIPTION OF THE PREFERRED EMBODIMENTS

Reference will now be made in detail to embodiments of the invention. Wherever possible, same or similar reference numerals are used in the drawings and the description to refer to the same or like parts or steps. The drawings are in simplified form and are not to precise scale. The word 'couple' and similar terms do not necessarily denote direct and immediate connections, but also include connections through intermediate elements or devices. For purposes of convenience and clarity only, directional (up/down, etc.) or motional (forward/back, etc.) terms may be used with respect to the drawings. These and similar directional terms should not be construed to limit the scope in any manner. It will also be understood that other embodiments may be utilized without departing from the scope of the present invention, and that the detailed description is not to be taken in a limiting sense, and that elements may be differently positioned, or otherwise noted as in the appended claims without requirements of the written description being required thereto.

Various operations may be described as multiple discrete operations in turn, in a manner that may be helpful in understanding embodiments of the present invention; however, the order of description should not be construed to imply that these operations are order dependent.

It will be further understood by those of skill in the art that the apparatus and devices and the elements herein, without limitation, and including the sub components such as operational structures, circuits, communication pathways, and related elements, control elements of all kinds, display circuits and display systems and elements, any necessary driving elements, inputs, sensors, detectors, memory elements, processors and any combinations of these structures etc. as will be understood by those of skill in the art as also being identified as or capable of operating the systems and devices and subcomponents noted herein and structures that accomplish the functions without restrictive language or label requirements since those of skill in the art are well versed in related X-Ray diagnostic devices, computer and operational controls and technologies of radiographic devices and all their sub components, including various circuits and combinations of circuits without departing from the scope and spirit of the present invention.

As used herein, a "detector" or an "element" in the devices comprises generally the physical and electronic components, physical structures and features sensors and outputs necessary to receive information in data form (for received data), a detecting or determining mechanism to determine the result of the received data, an output device for outputting data in tangible form (e.g. printing or displaying on a computer screen or transmitting code specific data to a further structure in the system or device), optionally a permanent memory for storing data as well as computer code related operational control code, and also optionally a microprocessor for executing computer code wherein said computer code resident in said permanent memory for the detector.

Embodiment 1

Referring to Figures, the inventors set forth the Embodiment 1 of the present invention.

Figure 1:
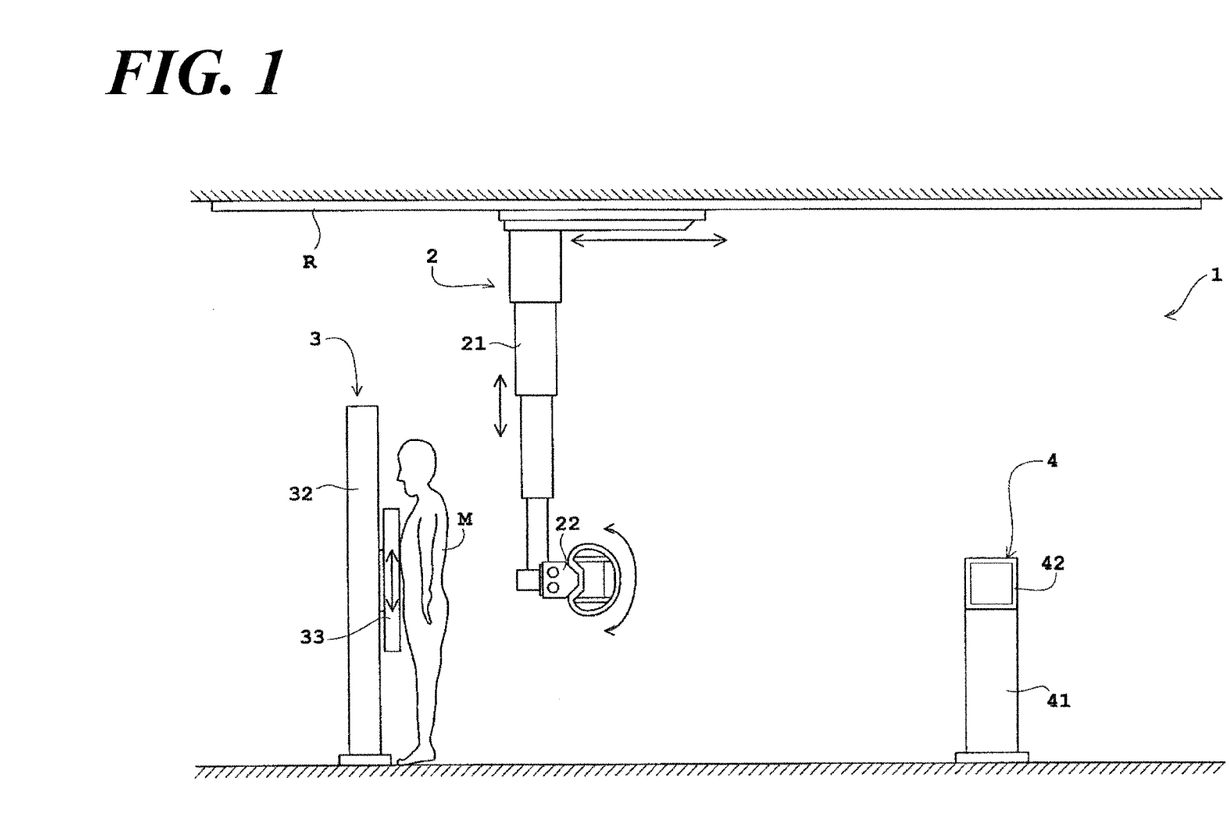
FIG. 1 is a schematic view illustrating an X-ray diagnostic device according to the aspect of each Embodiment when an X-ray imaging unit is the standing position X-ray imaging stand.

FIG. 1 is the schematic view illustrating the X-ray diagnostic device according to the aspect of each Embodiment when the X-ray imaging unit is the standing position X-ray imaging stand.

FIG. 2 is the schematic view and the block diagram illustrating the X-ray imaging device according to the aspect of the Embodiment 1.

Figure 3A:
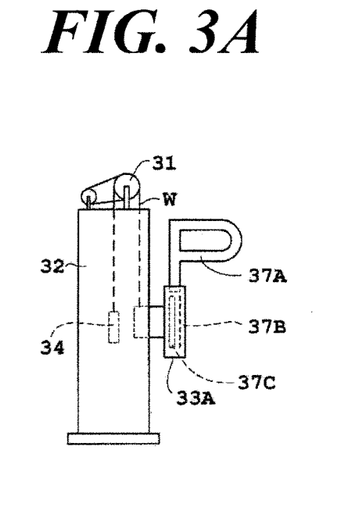
FIG. 3A is a view illustrating one Embodiment of an up-and-down moving element and an attachment-and-detachment member when the X-ray imaging unit is the standing position X-ray imaging stand.

FIG. 3A is the view illustrating one Embodiment of the up-and-down moving element and the attachment-and-detachment member when the X-ray imaging unit is the standing position X-ray imaging stand.

Figure 3B:
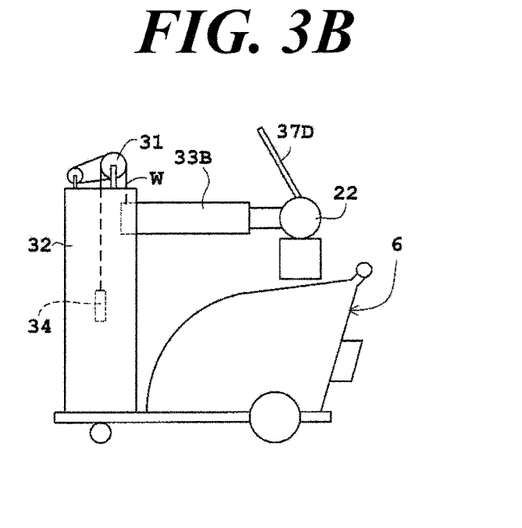
FIG. 3B is a view illustrating one Embodiment of the up-and-down moving element and an attachment-and-detachment member when the X-ray imaging unit and the X-ray tube therefor is for a mobile medical unit.

FIG. 3B is the view illustrating one Embodiment of the up-and-down moving element and the attachment-and-detachment member when the X-ray imaging unit and the X-ray tube therefor is for the mobile medical unit.

Figure 4:
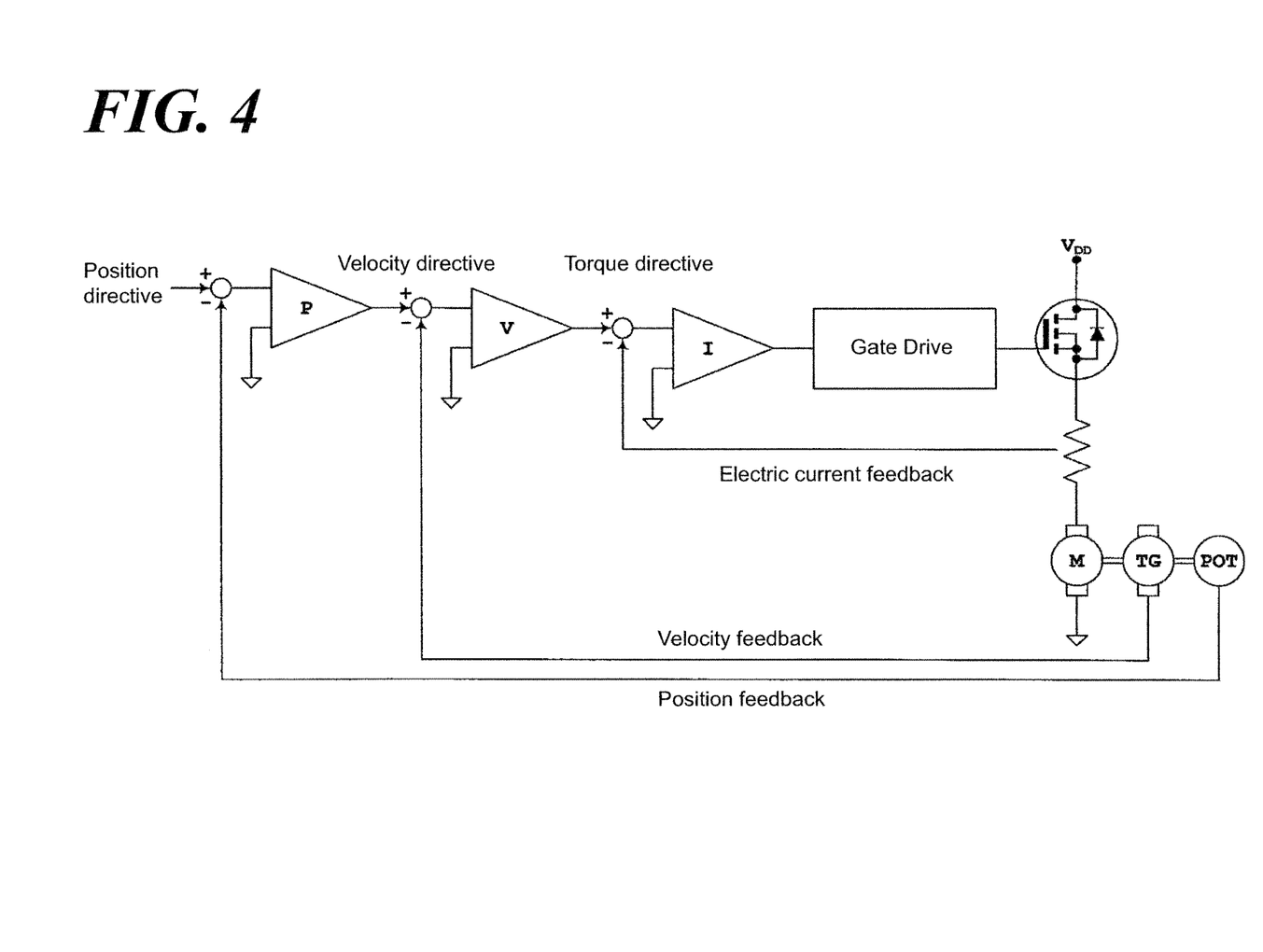
FIG. 4 is a circuit view illustrating a motor control circuit of a rotation detection element, a torque adjustment element and a torque detection element of an X-ray imaging unit according to the aspect of the Embodiment 1 and 2.

FIG. 4 is the circuit view illustrating the motor control circuit of the rotation detection element, the torque adjustment element and the torque detection element of the X-ray imaging unit according to the aspect of the Embodiment 1 and 2. The inventors set forth the device to perform an X-ray imaging as an example of the X-ray diagnostic device according to the aspect of the Embodiment 1, including the Embodiment 2 and 3 described later.

Referring to FIG. 1, when the X-ray imaging unit is the standing position X-ray imaging stand, the X-ray diagnostic device comprises an X-ray tube unit 2, an X-ray imaging unit 3 and a display operation unit 4. When the X-ray imaging unit 3 is the standing position X-ray imaging stand, the X-ray tube unit 2 comprises an X-ray hanging unit, by which the X-ray tube 22 is movably hung and held along the ceiling. In addition, the X-ray imaging unit 3 comprises the standing position X-ray imaging stand that performs an X-ray imaging while a subject M is in the standing posture. The X-ray tube unit 2, the X-ray imaging unit 3 and the display operation unit 4 are electrically connected through a communication cable (not shown in FIG.) each other and the X-ray tube unit 2, the X-ray imaging unit 3 and the display operation unit 4 are communicable with the communication cable each other. The X-ray diagnostic device 1 corresponds to the X-ray diagnostic device of the present invention.

Referring to FIG. 1, when the X-ray imaging unit 3 is the standing position X-ray imaging stand, the X-ray tube unit 2 comprises: a movable along the ceiling and vertically telescopic support arm 21; and an X-ray tube 22 supported by the support arm 21 and capable of adjusting the facing direction thereof. Referring to FIG. 1, when the X-ray imaging unit 3 is the standing position X-ray imaging stand, the X-ray imaging unit 3 supports the subject M in the standing posture. The specific structure of the X-ray imaging unit 3 is set forth later referring to FIG. 2 and FIG. 3. A display-operation unit 4 comprises: an operation panel 41 that comprehensively controls each unit or is operated by an operator; and a monitor 42 that displays the X-ray image.

When the X-ray imaging unit 3 is the standing position X-ray imaging stand, the support arm 21 of the X-ray tube unit 2 is movable along the rail R installed on the ceiling. Referring to FIG. 1, the rail R is also installed in the depth direction of the paper and the support arm 21 is also movable in the depth direction of the paper. The support arm is telescopic, i.e., extendable and retractable, and the X-ray tube 22 is supported by the support arm 21, so that the X-ray tube 22 is movable horizontally and vertically. In addition, the facing direction of the X-ray tube 22 is adjustable. Accordingly, referring to FIG. 1, the X-ray imaging in the standing posture can be performed by adjusting the face of the X-ray tube 22 toward the standing position X-ray imaging stand of the X-ray imaging unit 3 by moving horizontally and vertically. In addition, even not shown in FIG., when the lying position table unit having the lying position table on which the subject M is loaded in the lying posture is arranged, the X-ray imaging in the lying posture can be also performed by adjusting the face of the X-ray tube 22 toward the standing position X-ray imaging stand of the X-ray imaging unit 3 by moving horizontally and vertically.

The operation panel of the display-operation unit 41 comprises input a control element such as a central processing unit (CPU) and an input element operated by an operator. The control element controls comprehensively each unit through the above communication cable. The control element operates each unit by sending the data and the command input by the operator through the communication cable. Referring to FIG. 3A, a monitor 42 of the display-operation unit 4 displays the X-ray image acquired by the X-ray detector 37C, set forth later, through the above communication cable.

Referring to FIG. 2, according to the aspect of the Embodiment 1, the X-ray imaging unit 3 comprises; a pulley 31, a pulley holding element 3 (also referring to FIG. 1), a up-and-down moving element 33 (also referring to FIG. 1), a counterweight 34, a motor 35, a brake 36 and an attachment-and-detachment member 37. Further, the X-ray imaging unit 3 comprises; an attachment-and-detachment detection element 38, a rotation detection element 39, a torque adjustment element 51 and a torque detection element 52. The pulley 31 corresponds to the pulley of the present invention, the pulley holding element 32 corresponds to the pulley holding means of the present invention, the up-and-down moving element 33 corresponds to the up-and-down moving means, the counterweight 34 corresponds to the counterweight of the present invention, the motor 35 corresponds to the motor of the present invention, the brake 36 corresponds to the brake of the present invention, the attachment-and-detachment member 37 corresponds to the attachment-and-detachment member of the present invention, the attachment-and-detachment detection element 38 corresponds to the attachment-and-detachment detection means of the present invention, the rotation detection element 39 corresponds to the rotation detection means of the present invention, the torque adjustment element 51 corresponds to the torque adjustment means of the present invention, and the torque detection element 52 corresponds to the torque detection means of the present invention.

The pulley 31 is held at the upper portion of the pulley holding element 32, so that the pulley holding means 32 can hold the pulley 31. The up-and-down moving element 33 is held as freely movable by the wire W from the pulley 31 in the up-and-down direction (the direction indicated by the arrow referring to FIG. 1 and FIG. 3). The counterweight 34 is connected to the wire W at the other end than the end of the up-and-down element 33 and provides the up-and-down moving element 33 with a weight-balance through the pulley 31. Specifically, the up-and-down moving element 33 and the counterweight 34 are being hung by the wire W, so that the balance can be kept.

The pulley 31 connects the motor 35, so that the pulley 31 can be driven to rotate by the motor 35. In addition, the brake 36 to suspend the rotation of the pulley 31 is equipped. In addition, the attachment-and-detachment member 37 is mounted to the up-and-down moving element 33, so that the attachment-and-detachment member 37 can be attached to and detached from the up-and-down element 33. The attachment-and-detachment detection element 38 detects the attachment-and-detachment of the attachment-and-detachment member 37.

The pulley holding element 32 is a support column made of e.g., metal. Referring to FIG. 3A, the up-and-down moving element 33 is a Bucky element 33A, e.g., when the X-ray imaging unit 3 is the standing position X-ray imaging stand; and referring to FIG. 3B, the up-and-down moving element 33 is the X-ray holding arm 33B, e.g., when the X-ray imaging unit 3 and the X-ray tube unit 2 are for the mobile medical units. In addition, in the case of the mobile medical unit, the pulley holding element 32 including the support column is mounted to the wheeled platform 6.

The counterweight 34 is e.g., a lead lump. According to the aspect of the present Embodiment 1, including also the Embodiment 2 and 3 set forth later, when the attachment-and-detachment member 37 is mounted to the up-and-down moving element 33, the weight of the counterweight 34 is set as both weights of the up-and-down element 33 and the attachment-and-detachment member 37 are balanced each other. In addition, when the attachment-and-detachment member 37 is detached and only the up-and-down moving element 33 is left, the weight of the counterweight 34 can be set as only the weight of the up-and-down moving element 33 is balanced. However, when the X-ray imaging is performed, the attachment-and-detachment member 37 is attached to the up-and-down moving element 33 in many cases, and therefore, if the weight of the counterweight 34 is set as the weight due to only up-and-down moving element 33 is balanced, at least one selected from the group consisting of the pully 31, the up-and-down moving element 33 and the counterweight 34 must be locked by the brake 36 to suspend up-and-down move of the up-and-down moving element 33 when the X-ray imaging is performed. Therefore, it is preferred that the weight of the counterweight 34 is set so as to balance the weight of the up-and-down moving element 33 and the weight of the attachment-and-detachment member 37 so that the locking by the brake 36 can be avoided when the X-ray imaging is performed. Needless to say, if the attachment-and-detachment member 37 is detached and only the up-and-down moving element 33 is mounted when the X-ray imaging is performed, the weight of the counterweight 34 can be set so as to balance only the weight of the up-and-down moving element 33.

The motor 35 is e.g., an AC servomotor. The brake is e.g., the compound magnet of a permanent magnet and an electromagnet (permanent-electro-magnet). Referring to FIG. 3A, when e.g., the X-ray imaging unit 3 is a standing position X-ray imaging stand, the attachment-and-detachment member 37 includes a grip bar 37A that the subject as a patient grips when taking the X-ray imaging, a scattered X-ray removal grid 37B, or an X-ray detector 37C; and referring to FIG. 3B, when e.g., the X-ray imaging unit 3 and the X-ray tube unit 2 are mounted to the mobile medical unit, the attachment-and-detachment member 37 includes a tablet PC (PC: Personal Computer) 37D in order to display and input a variety of data.

The X-ray detector 37C is e.g., a flat panel X-ray detector or an X-ray film cassette or IP (imaging plate) cassette. The X-ray detector 37C detects the X-ray transmitted through the subject M and then outputs the X-ray image thereof to send to the monitor 42 of the display-operation unit to display. Or the X-ray image can be printed out. The attachment-and-detachment member 38 is e.g., a contact switch such as a micro switch or a non-contact switch such as a photo sensor or a magnetic sensor.

The rotation detection element 39 detects the rotation of the motor 35. The torque adjustment element 51 adjusts the torque of the motor 35. The torque detection element 52 detects the torque when the rotation of the motor 35 suspends. The rotation detection element 39, the torque adjustment element 51 and the detector 52 comprise a control circuit, and the control circuit therefor further comprises e.g., a motor control circuit referring to FIG. 4. For example, the servoamp MR-J3 series available from Mitsubishi can be used as the motor control circuit.

Referring to FIG. 4, in the motor control circuit, a positional amplifier (indicated by P in FIG. 4), a velocity amplifier (indicated by v in FIG. 4), and an electric current amplifier (indicated by I in FIG. 4) are connected in series and a gate drive and then a transistor are connected down the stream to the electric current amplifier in order. The transistor is connected to the motor (indicated by M in FIG. 4) via the electric current resistance (indicated by R in FIG. 4), and the motor is connected to a tachogenerator (indicated by TG in FIG. 4) further connected to a potentiometer (indicated by POT in FIG. 4). The position detected by the potentiometer is subjected to the feedback control (positional feedback) relative to the position amplifier, the velocity of the motor (rotation rate) detected by the tachogenerator is subjected to the feedback control (velocity feedback) relative to the velocity amplifier and the electric current corresponding to the rotation torque detected by the electric current detection resistance is subjected to a feedback control (electric current feedback) relative to the electric current amplifier.

In such way, referring to FIG. 4, the tachogenerator or the potentiometer correspond to the rotation element 39, and the tachogenerator or the potentiometer detects the rotation of the motor 35 (referring to FIG. 2). The electric current amplifier of the torque directive corresponds to the torque adjustment element 51 to adjust the torque of the motor 35. The electric current detection resistance corresponds to the torque detection element 52 and when the rotation of the motor 35 suspends, the torque (here, the electric current corresponding to the rotation torque) is detected.

Referring to FIG. 2, the inventors set forth the control of the motor 35. At the same time when the attachment-and-detachment detection element 38 detects the update (attachment or detachment) of the attachment-and-detachment state of the attachment-and-detachment member 37, the variation of the weight of the up-and-down moving element 33 along the state of the attachment-and-detachment varies. Such variation of the weight indicates the weight-balance between the up-and-down moving element 33 and the counterweight 34 has become out of balance. The attachment-and-detachment detection element 38 detects the incident of the out of balance and such detection works as the trigger to release the brake 36.

Then, the up-and-down moving element 33 moves either upward or downward due to out of weight-balance (i.e., unbalanced), so that both the pulley 31 and the motor 35 rotate at the same time. Then, the rotation detection element 39 (tachogenerator or potentiometer in FIG. 4) detects the rotation of the motor 35. For example, referring to FIG. 4, if the velocity directive is null, the feedback control is operative not to rotate the motor 35 and the torque not to rotate is instantly determined by the torque adjustment element 39 (electric current amplifier in FIG. 4) and the motor 35 suspends, accordingly. Specifically, the balance is in the libratory state (balance is kept). At this time, the torque detection element 52 (electric current detection resistance in FIG. 4) detects the torque and such torque is provided continuously for the motor 35 while being kept until the next update of attachment-and-detachment state so that the balance between the up-and-down moving element 33 and the counterweight 34 can be kept and the rest state can be kept despite release of the brake.

In the X-ray imaging apparatus 1 according to the aspect of the present Embodiment 1, the attachment-and-detachment element 38 detects out of weight-balance between the up-and-down moving element 33 and the counterweight 34 by attachment-and-detachment of the attachment-and-detachment member 37. When the attachment-and-detachment is detected by the attachment-and-detachment detection element 38 under releasing the brake 36 (suspend the rotation of the pulley 31), the motor 35 (to drive the pulley 31) rotates along with rotation of the pulley 31 due to the above out of weight-balance (i.e., out of balance). At this time, the rotation detection element 39 to detect rotation of the motor 35 and the torque adjustment element 51 are equipped, so that the torque adjustment element 51 adjusts the torque of the motor 35 so as to suspend the rotation of the motor 35 detected by the rotation detection element 39. In addition, the torque detection element 52 that detects torque when the motor 35 suspends is equipped and the torque when the rotation of the motor 35, which is detected by the torque detection element 52, is continuously provided for the motor 35, so that the balance between the up-and-down moving element 33 and the counterweight 34 can be kept.

In such way, even though any member of the attachment-and-detachment members 37 is either attached or detached, it is not necessary for the moving to be locked because of the out of balance between the up-and-down moving element 33 and the counterweight 34 and when the moving is allowed under the out of balance, uncontrollable moving of the up-and-down moving element 33 may not expose the operator and the patient subject to risk and further a light work can be operational. In addition, when the attachment-and-detachment member 37 is attached to or detached from the up-and-down moving element 33, the torque can be adjusted arbitrarily (as the rotation of the motor 35 suspends) corresponding to the weight, the kind and the number of the attachment-and-detachment member, so that the weight, the kind and the number of the attachment-and-detachment members to be attached or detached may not be mandatory to be figured out in advance (ii) (iii). In addition, the rotation of the motor 35 suspends by adjusting the torque and the balance can be kept, so that the mechanism cannot be bulky (i) because a large diameter of the rotation unit is not required to be assured or the diameter update mechanism is not required as required in conventional ways. In addition, as the torque can be adjusted regardless the difference between individuals so that the rotation of the motor 35 suspends and the balance is being kept, no calibration is required unit by unit (iv). As results, no bulky mechanisms is required (i); the weight, the kind and the number of the attachment-and-detachment members to be attached and detached is not mandatory to be figured out in advance (ii) (iii); and no calibration is required unit by unit (iv).

According to the aspect of the present Embodiment 1, the motor 35 and the control circuit thereof (the rotation detection element 39, the torque adjustment element 51 and the torque detection element 52) are only required to be equipped, so that the apparatus size can be small and even if a variety of members (attachment-and-detachment members) having different weight each other are attached or detached, the balance can be always kept without problem. Accordingly, when the operator releases manually the brake 36, the up-and-down moving element 33 does not uncontrollably move due to out of balance to be risky for the operator and the subject or loading due to increase of operations because of out of balance would not increase, and under the out of balance, the motor 35 covers the out of balance, so that the lock can be released.

Embodiment 2

Next, referring to FIGs, the inventor sets forth the Embodiment 2 of the present invention.

Figure 5:
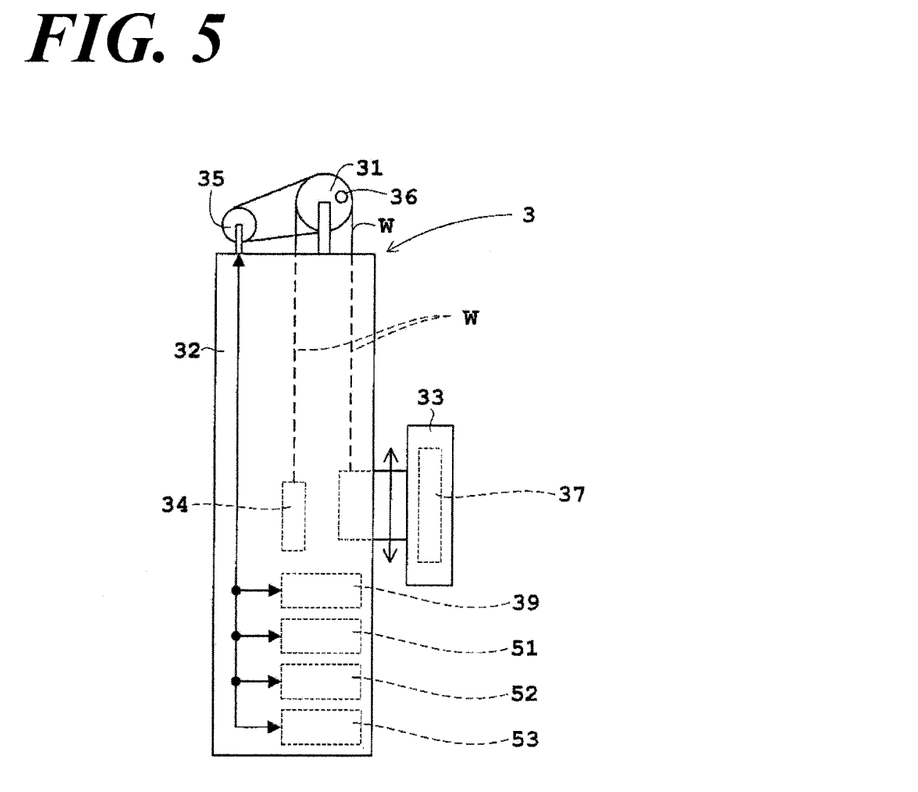
FIG. 5 is a schematic view and a block diagram illustrating an X-ray imaging device according to the aspect of the Embodiment 2.

FIG. 5 is a schematic view and a block diagram illustrating the X-ray imaging unit of the X-ray imaging device according to the aspect of the Embodiment 2. The same portion as the above Embodiment 1 is indicated by the same sign and the illustration thereof is omitted and is not shown in FIG. In addition, when the X-ray imaging unit is the standing position X-ray imaging stand, even according to the Embodiment 2, the X-ray diagnostic device comprises the same components referring to FIG. 1 and FIG. 3A, and when the X-ray imaging unit and the X-ray tube unit are for the mobile medical device, the X-ray diagnostic device comprises the same components as indicated in FIG. 3B even according to the aspect of the present Embodiment 2.

According to the aspect of the above Embodiment 1, the attachment-and-detachment detection element 38 (referring to FIG. 2) is equipped, but according to the aspect of the present Embodiment 2, a timer 53 is equipped instead of the attachment-and-detachment detection element referring to FIG. 5. Specifically, according to the aspect of the Embodiment 1, the trigger to make sure the balance is the detection data from the attachment-and-detachment detection element 38; but according to the aspect of the present Embodiment 2, the timer 53 sets the trigger (i.e., when the brake release and brake operation are repeated periodically, the timer 53 sets the trigger periodically), which is a different point from the aspect of the Embodiment 1. The timer 53 corresponds to the timer of the present invention.

In addition, also according to the aspect of the present Embodiment 2, the rotation detection element 39, the torque adjustment element 51 and the detector 52 comprise a control circuit to control the motor 35, and the control circuit therefor comprises e.g., a motor control circuit referring to FIG. 4.

According to the aspect of the present Embodiment 2, the weight balance is not always required to be kept (i.e., weights are being libratory). The brake release and the brake operation with the brake 36 are conducted in order. When the brake release and the brake operation are multiply repeated, the brake release and the brake operation with the brake 36 are periodically repeated. The number of repeats of the brake release and the brake operation is not particularly limited, and the brake release and the brake operation may be conducted in order at once or the brake release and the brake operation may be multiply repeated.

The time period of the brake release is also not particularly limited. For example, if the brake releasing time is set as approximately 2 seconds, the up-and-down moving element 33 would not move either upward or downward and even due to the out of balance when the brake is released the motor 35 rotates and the rotation detection element 39 can detect the rotation thereof. However, if the brake releasing time is too long, the up-and-down moving element 33 moves upward and collides against the pulley 31, or the up-and-down moving element 33 moves downward and collides against the floor surface. If the time is vice versa too short, the rotation detection element 39 can hardly detect rotation of the motor 35. Accordingly, the brake releasing time can be adequately set depending on the weight of the up-and-down element 33 and the weight of the counterweight 34 and the weight of the attachment-and-detachment member 37 and so forth.

The timer 53 monitors the time when the brake 36 is temporarily released. And the rotation detection element 39 detects the rotation of the motor 35 along with the rotation of the pulley 31 due to out of balance between the up-and-down moving element 33 and the counterweight 34 when the timer 53 releases the brake. In such way, the timer 53 sets the trigger.

When the rotation detection element 39 detects the rotation of the motor 35, as wells as the above described Embodiment 1, the motor 35 is subjected to feedback control not to rotate and the torque is instantly determined not to rotate by the torque adjustment element 39 and the motor 35 suspends. Specifically, the balance is in the balanced state (the balance is kept). At this time, the torque detection element 52 detects the torque and such torque is provided continuously for the motor 35 while being kept until the next update of attachment-and-detachment state so that the balance between the up-and-down moving element 33 and the counterweight 34 can be kept and the rest state can be kept despite release of the brake 36.

When the brake release and the brake operation are conducted only once in order for the brake release and the brake operation; the rotation detection element 39 detects the rotation of the motor 35, when the brake is released, the motor 35 is subjected feedback control not to rotate, the torque adjustment element 51 determines the torque not to rotate, and the respective torques are continuously provided for the motor 35 while the respective torques are being kept until the next updated attachment-and-detachment state. On the other hand, when the brake release and the brake operation are conducted multiple times, the rotation detection element 39 detects the respective rotations of the motor 35, when the brake is respectively released, the motor 35 is subjected to feedback control not to rotate every respective detections, the torque adjustment element 39 determines the torque not to rotate every respective detections, and the respective torques are continuously provided for the motor 35 while the respective torques are being kept until next cycle.

In the X-ray imaging apparatus according to the aspect of the present Embodiment 2, without equipping the attachment-and-detachment detection element 38 (referring to FIG. 2) according to the aspect of the Embodiment 1 is not equipped, which is different from the above Embodiment 1, the brake release and the brake operation are conducted in order. Accordingly, when the brake is released, the motor (to drive the pulley 31) also rotate along with the rotation of the pulley 31 due to the out of balance between the up-and-down moving element 33 and the counterweight 34. Then as well as the Embodiment 1, the rotation detection element 39 to detect rotation of the motor 35 and the torque adjustment element 51 are equipped, so that the torque adjustment element 51 adjusts the torque of the motor 35 so as to suspend the rotation of the motor 35 detected by the rotation detection element 39. In addition, as well as the Embodiment 1, when the rotation of the motor 35 suspends, the torque detection element 52 that detects the torque at that time is equipped, so that the torque at which the rotation of the motor 35 detected by the torque detection element 52 suspends can be provided continuously for the motor 35 and the balance between the up-and-down moving element 33 and the counterweight 34 can be kept, accordingly.

Accordingly and differently from the Embodiment 1, when the brake is released, even if the motor 35 and the pulley 31 rotate due to the out of balance between the up-and-down moving element 33 and the counterweight 34, the torque is adjusted so as to suspend the rotation of the motor 35, and the adjusted torque is continuously provided for the motor 35, so that the balance can be kept. In such way, it is not necessary for the moving to be locked because of the out of balance between the up-and-down moving element 33 and the counterweight 34 and when the moving is allowed under the out of balance as well as the Embodiment 1, uncontrollable moving of the up-and-down moving element 33 may not expose the operator and the patient subject M to risk and further a light work can be operational. In addition, when the brake is released, the torque can be adjusted arbitrarily (as the rotation of the motor 35 suspends) corresponding to the weight, the kind and the number of the attachment-and-detachment member 37, so that the weight, the kind and the number of the attachment-and-detachment members 33 to be attached thereto and detached therefrom may not be mandatory to be figured out in advance (ii) (iii) as well as the Embodiment 1. In addition, as well as the Embodiment 1, rotation of the motor suspends by adjusting the torque and the balance can be kept, so that the mechanism cannot be bulky (i) because a large diameter of the rotation unit is not required to be assured or the diameter update mechanism is not required as required in conventional ways. In addition, as the torque can be adjusted regardless the difference between individuals so that the rotation of the motor 35 suspends and the balance is being kept, no calibration is required unit by unit (iv). As results, no bulky mechanisms is required (i), the weight, the kind and the number of the attachment-and-detachment members 37 to be attached and detached is not mandatory to be figured out in advance (ii) and no calibration is required unit by unit (iv).

Even when an operator provides the initiation directive to release the brake and, at the same time, the rotation detection element 39 can be operative to detect the rotation of the motor 35, but a time-lag may take place between the initiation directive to release the brake and the detection of the rotation of the motor 35 by the rotation detection element 39. Therefore, according to the aspect of the present Embodiment 2, it is preferred that the timer 53 that monitors the time when the brake 36 is temporarily released is equipped and the rotation detection element 39 detects the rotation of the motor 35 along with the rotation of the pulley 31 due to out of balance between the up-and-down moving element 33 and the counterweight 34 when the brake is released by the timer 53. If such timer 53 is equipped, an incident of the time-lag can be prevented and the balance holding can be more preciously controlled.

Embodiment 3

Next, referring to FIGs, the inventors set forth the Embodiment 3 of the present invention.

Figure 6:
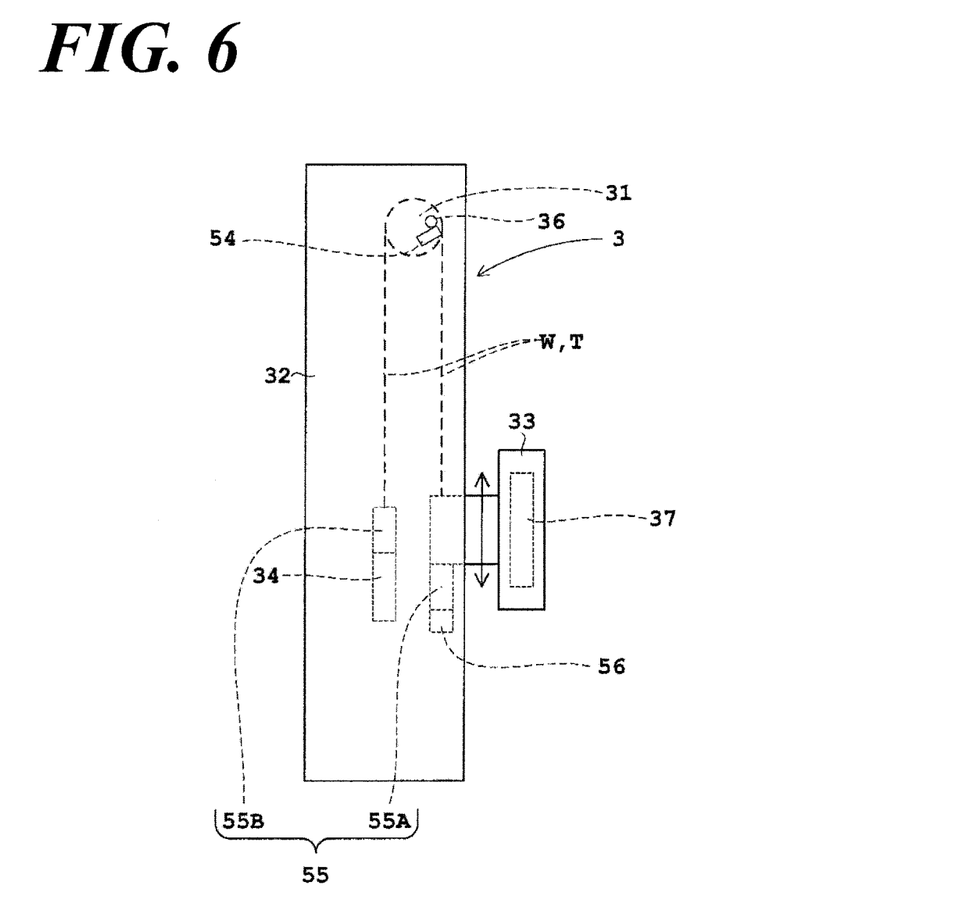
FIG. 6 is a schematic view and a block diagram illustrating an X-ray imaging device according to the aspect of the Embodiment 3.

FIG. 6 is the schematic view and the block diagram illustrating the X-ray imaging device according to the aspect of the Embodiment 3. The same portion as the above Embodiment 1, 2 is indicated by the same sign and the illustration thereof is omitted and is not shown in FIG. In addition, when the X-ray imaging unit is the standing position X-ray imaging stand, even according to the Embodiment 3, the X-ray diagnostic device comprises the same components referring to FIG. 1 and FIG. 3A, and when the X-ray imaging unit and the X-ray tube unit are for the mobile medical device, the X-ray diagnostic device comprises the same components as indicated in FIG. 3B even according to the aspect of the present Embodiment 3.

According to the aspect of the above Embodiment 1, the attachment-and-detachment detection element 38 (referring to FIG. 2) is equipped and according to the aspect of the above Embodiment 1, 2, the rotation detection element 39 and the torque adjustment element 51 and the torque detection element 52 (referring to FIG. 2 and FIG. 5) are equipped, but according to the aspect of the Embodiment 3, a loading weight detection element 54, a tank 55 and a pump 56, referring to FIG. 6, are equipped instead of the attachment-and-detachment detection element, the rotation detection element, the torque adjustment element and the torque detection element. The loading weight detection element 54 corresponds to the loading weight detection means of the present invention, the tank 55 corresponds to the tank of the present invention and the pump 56 corresponds to the pump of the present invention.

The loading weight detection element 54 detects the weight variation due to attachment-and-detachment of the attachment-and-detachment member 37. The loading weight detection element 54 is e.g., a strain gage. The tank 55 provides weight variation in association with the up-and-down moving element 33 and the counterweight 34 and contains fluid. In the present Embodiment 3, the inventors set forth liquid as the fluid.

The tank 55 comprises two tanks 55A and 55B, and the tank 55A is set in the side of the up-and-down moving element 33 and the tank 55B is set in the side of the counterweight 34. A tube T is set between the tank 55A located in the up-and-down moving element side and the tank 55B located in the counterweight side and the pump 56 transfers the liquid inside the tank 55 between the tank 55A located in the up-and-down moving element side and the tank 55B located in the counterweight side. The tube T is set along the wire W.

The tank 55 is e.g., made of polyethylene. The pump 56 is e.g., a plunger pump. The liquid inside the tank 55 is e.g., sodium polytungstate aqueous solution. A kind of the liquid is not particularly limited, but from a space saving standpoint, it is preferred to use the liquid having a larger specific gravity than water and the sodium polytungstate aqueous solution described above is suitable.

When the loading detection element 54 detects the weight variation due to attachment-and-detachment of the attachment-and-detachment member 37, the pump 56 is driven to flow the liquid in the direction to set off the weight variation between two tanks 55A and 55B, so that the balance between the up-and-down moving element 33 and the counterweight 34 can be kept. Specifically, the pump 56 is activated corresponding to the weight variation detected by the loading weight detection element 54 and the liquid in the tanks 55A and 55B is transferred inside the tube T so that the weight-balance can be maintained.

The X-ray diagnostic device 1 according to the aspect of the present Embodiment 3 comprises no attachment-and-detachment detection element 38 according to the aspect of the Embodiment 1 (referring to FIG. 2), differently from the Embodiment 1, 2 described above, and further comprises no rotation detection element 39 and no torque adjustment element 51 and no torque detection element 52 (referring to FIG. 2 and FIG. 5), but comprises the loading weight detection element 54 that detects the weight variation due to the attachment-and-detachment of the attachment-and-detachment member 37. Accordingly, the loading weight detection element 54 detects out of weight-balance between the up-and-down moving element 33 and the counterweight 34 due to the attachment-and-detachment of the attachment-and-detachment member 37. Then, differently from the Embodiment 1, 2, the tank 55 that provides weight variation in association with the up-and-down moving element 33 and the counterweight 34; and the pump 56 that transfers the fluid inside the tank 55 (liquid according to the aspect of the present Embodiment 3) between the tank 55A located in the up-and-down moving element 33 side and the tank 55B located in the counterweight 34 side; are equipped. Further, when the loading weight detection element 54 detects the weight variation due to the attachment-and-detachment of the attachment-and-detachment member 37, the pump 56 is driven to flow the liquid in the direction to set off the weight variation between two tanks 55A and 55B so that the balance between the up-and-down moving element 33 and the counterweight 34 can be kept.

In such way, differently from the Embodiments 1, 2, the pump 56 is activated corresponding to the weight variation detected by the loading weight detection element 54 to flow the fluid (liquid) in the direction to set off the weight variation between two tanks 55A and 55B so that the balance can be kept. Accordingly, as well as the Embodiment 1, even if any attachment-and-detachment member 37 is attached or detached, it is not necessary for the moving to be locked because of the out of balance between the up-and-down moving element 33 and the counterweight 34 and when the moving is allowed under the out of balance, uncontrollable moving of the up-and-down moving element 33 may not expose the operator and the patient subject M to risk and further a light work can be operational. In addition, the fluid (liquid) moves corresponding to weight variation, so that the weight, the kind and the number of the attachment-and-detachment members 33 to be attached thereto and detached therefrom may not be mandatory to be figured out in advance (ii) (iii) as well as the Embodiment 1, 2. In addition, the fluid (liquid) moves corresponding to weight variation and the balance can be kept, so that the mechanism cannot be bulky (i) because a large diameter of the rotation unit is not required to be assured or the diameter update mechanism is not required as required in conventional ways. In addition, the fluid (liquid) moves corresponding to the weight variation and the balance can be kept regardless the difference between individuals, so that no calibration is required unit by unit (iv). As results, no bulky mechanisms is required (i); the weight, the kind and the number of the attachment and detachment members to be attached or detached is not mandatory to be figured out in advance (ii) (iii); and no calibration is required unit by unit (iv) as well as the Embodiment 1, 2.

Referring to FIG. 6, the motor 35 (referring to FIG. 2 and FIG. 5) is not equipped. Accordingly, the pulley 31 can be embedded to be held in the pulley holding element 32. Needless to say, the pulley 31 can be held in the upper part of pulley holding element 32. In addition, a motor can be equipped so that the up-and-down moving element 33 and the counterweight 34 can be moved supplementarily by driving the motor.

The present invention is not limited to the aspect of the Embodiments set forth above and further another alternative Embodiment can be implemented set forth below.

(1) According to the above Embodiments, the inventors set forth an X-ray imaging apparatus as an example of the X-ray diagnostic device, but the invention is not limited to such X-ray imaging apparatus. If the apparatus could hold the balance (counterbalance) with a wire and a counterweight and could conduct an X-ray diagnosis, for example, the present invention can be applied to an X-ray fluoroscopic apparatus that irradiates weaker radiation than the X-ray imaging to acquire a plurality of images successively and displays each real-time X-ray image (video display).

(2) According to the above each Embodiment, the inventors set fort each component according to the aspect of each Embodiment is independent each other, but each component according to the aspect of each Embodiment can be combined. For example, in the combination of the Embodiment 1 and the Embodiment 2, either the mode according to the aspect of the Embodiment 1 or the mode according to the aspect of the Embodiment 2 can be arbitrarily selected. In addition, in the combination of the Embodiment 1 and the Embodiment 3, either the mode according to the aspect of the Embodiment 1 or the mode according to the aspect of the Embodiment 3 can be arbitrarily selected. In addition, in the combination of the Embodiment 2 and the Embodiment 3, either the mode according to the aspect of the Embodiment 2 or the mode according to the aspect of the Embodiment 3 can be arbitrarily selected. Further, in the combination of the Embodiment 1 and the Embodiment 3, either the mode according to the aspect of the Embodiment 1, the mode according to the aspect of the Embodiment 2 or the mode according to the aspect of the Embodiment 3 can be arbitrarily selected:

(3) According to the above each Embodiment, the control element such as a central processing unit (CPU) and so forth is independently equipped from the X-ray imaging unit 3 (referring to FIG. 2, FIG. 5, FIG. 6), but such control element can be incorporated in the X-fray imaging unit 3.

(4) According to the above Embodiment 2, the timer that monitors the time when the brake is temporarily released is equipped and the rotation detection means (rotation detection element according to the Embodiment 2) detects the rotation of the motor along with the rotation of the pulley due to out of balance between the up-and-down moving means and the counterweight when the timer releases the brake, but the timer is not mandatory. If no time-lag takes place between the initiation directive of the brake release and the detection of the rotation of the motor by the rotation detection means (rotation detection element), the operator can direct the initiation of the brake release and at the same time, the detection of the rotation of the motor by the rotation detection means (rotation detection element) without equipping the timer.

(5) According to the above Embodiment 3, the fluid in the tank is a liquid as an example and sodium polytungstate aqueous solution having a larger specific gravity than water is applied as such liquid, but the fluid is not limited to liquid or the liquid having a larger specific gravity than water. The fluid can be gas (air, rare gas and nitrogen gas). However, from a space saving standpoint, it is preferred to use the liquid having a larger specific gravity than water.

FIELD OF THE INVENTION

As set forth above, the present invention is suitable for the standing position X-ray imaging stand and the mobile medical X-ray imaging apparatus.

REFERENCE OF SIGN

1 X-ray diagnostic device
31 Pulley
32 Pulley holding element
33 Up-and-down moving element
34 Counterweight
35 Motor
36 Brake
37 Attachment-and-detachment member
38 Attachment-and-detachment detection element
39 Rotation detection element
51 Torque adjustment element
52 Torque detection element
53 Timer
54 Loading weight detection element
55 Tank
56 Pump Having described at least one of the preferred embodiments of the present invention with reference to the accompanying drawings, it will be apparent to those skills that the invention is not limited to those precise embodiments, and that various modifications and variations can be made in the presently disclosed system without departing from the scope or spirit of the invention. Thus, it is intended that the present disclosure cover modifications and variations of this disclosure provided they come within the scope of the appended claims and their equivalents.

What is claimed is:

1. An X-ray diagnostic device, that perform X-ray diagnosis, comprising:
    a pulley;
    a pulley holding mechanism that holds said pulley;
    an up-and-down moving mechanism that is held freely movable in an up-and-down direction with a wire from said pulley;
    a counterweight that makes a weight-balance with said up-and-down moving mechanism through said pulley;
    wherein said counterweight is connected to one opposite end of said wire of which the other end is inside of said up-and-down moving mechanism;
    a motor that drives said pulley;
    a brake that suspends a rotation of said pulley; and
    an attachment-and-detachment member that is attached to and detached from said up-and-down moving mechanism; and
    further comprising:
        an attachment-and-detachment detection mechanism that detects an attachment-and-detachment of said attachment-and-detachment member;
        a rotation detection detector that detects a rotation of said motor;
        a torque adjustment system that adjusts a torque of said motor;
        a torque detection detector that detects the torque when a rotation of said motor suspends;
    wherein when said attachment-and-detachment mechanism detects an attachment-and-detachment event, said brake is released, said rotation detection detector detects the rotation of said motor along with the rotation of said pulley due to an out-of-balance event between said up-and-down moving mechanism and said counterweight when said attachment-and-detachment detection detector detects the attachment-and-detachment event, said torque adjustment system adjusts so as to suspend the rotation of said motor detected by said rotation detection detector, and the torque when the rotation of said motor detected by said torque detection detector suspends can be provided continuously, so that a balance between said up-and-down moving mechanism and said counterweight is kept.

2. An X-ray diagnostic device, that performs X-ray diagnosis, comprising:
   a pulley;
   a pulley holding mechanism that holds said pulley;
   an up-and-down moving mechanism that is held freely movable in an up-and-down direction with a wire from said pulley;
   a counterweight that makes a weight-balance with said up-and-down moving mechanism through said pulley;
   wherein said counterweight is connected to one opposite end of said wire of which an other end is inside side of said up-and-down moving mechanism;
   a motor that drives said pulley;
   a brake that suspends the rotation of said pulley; and
   an attachment-and-detachment member that is attached to and detached from said up-and-down moving mechanism; and
   further comprising:
      a rotation detection detector that detects a rotation of said motor;
      a torque adjustment system that adjusts a torque of said motor; and
      a torque detection detector that detects a torque when a rotation of said motor suspends;
   wherein a brake release and a brake operation are conducted in order, said rotation detection detector detects the rotation of said motor along with the rotation of said pulley due to an out-of-balance event between said up-and-down moving mechanism and said counterweight when the brake is released, said torque adjustment system adjusts so as to suspend the rotation of said motor detected by said rotation detection detector, and a torque when the rotation of said motor detected by said torque detection detector suspends can be provided continuously, so that a balance between said up-and-down moving mechanism and said counterweight is kept.

3. The X-ray fluoroscopic device, according to claim 2, comprising:
   a timer that monitors a time when said brake is temporarily released;
   wherein said rotation detection detector detects the rotation of said motor along with the rotation of said pulley due to said out-of-balance event between said up-and-down moving mechanism and said counterweight when said time releases the brake.

4. An X-ray diagnostic device, that perform X-ray diagnosis, comprising;
   a pulley;
   a pulley holding means that holds said pulley;
   an up-and-down moving mechanism that is held freely movable in an up-and-down direction with a wire from said pulley;
   a counterweight that makes a weight-balance with said up-and-down moving mechanism through said pulley;
   wherein said counterweight is connected to one opposite end of said wire of which an other end is inside of said up-and-down moving mechanism;
   a brake that suspends a rotation of said pulley; and
   an attachment-and-detachment member that is attached to and detached from said up-and-down moving mechanism; and
   further comprising:
      a loading weight detection detector that detects a weight variation due to an attachment-and-detachment event of said attachment-and-detachment member;
      a tank mechanism that provides a weight variation in association with said up-and-down moving mechanism and said counterweight; and
      a pump that transfers a fluid in said tank mechanism between a first tank located in an up-and-down moving mechanism side and a second tank located in the counterweight side;
   wherein when said loading weigh detection detector detects the weight variation due to attachment-and-detachment event of said attachment-and-detachment member, said pump is driven to flow the fluid in a direction to set off the weight variation between said first and second tanks, so that the balance between said up-and-down moving element and said counterweight can be kept.

* * * * *